US008684985B2

(12) United States Patent
Odoi

(10) Patent No.: US 8,684,985 B2
(45) Date of Patent: Apr. 1, 2014

(54) ABSORBENT ARTICLE HAVING ANGLED FLAPS

(75) Inventor: Haruko Odoi, Sakura (JP)

(73) Assignee: Daio Paper Corporation, Ehime (JP)

( * ) Notice: Subject to any disclaimer, the term of this patent is extended or adjusted under 35 U.S.C. 154(b) by 455 days.

(21) Appl. No.: 12/745,092

(22) PCT Filed: Nov. 26, 2008

(86) PCT No.: PCT/JP2008/071410
§ 371 (c)(1),
(2), (4) Date: Jun. 21, 2010

(87) PCT Pub. No.: WO2009/069634
PCT Pub. Date: Jun. 4, 2009

(65) Prior Publication Data
US 2010/0312215 A1    Dec. 9, 2010

(30) Foreign Application Priority Data

Nov. 27, 2007   (JP) ................................ 2007-305578

(51) Int. Cl.
*A61F 13/15*  (2006.01)
*A61F 13/20*  (2006.01)

(52) U.S. Cl.
USPC ............. 604/385.04; 604/385.03; 604/385.01

(58) Field of Classification Search
USPC ........................... 604/385.04, 385.03, 385.01
See application file for complete search history.

(56) References Cited

U.S. PATENT DOCUMENTS 5,401,268 A       3/1995  Rodier
6,652,701 B1 *   11/2003  Boulanger .................... 156/267

| 2005/0027276 | A1 * | 2/2005 | Collado et al. ........... 604/385.04 |
| 2005/0124959 | A1 * | 6/2005 | Alcantara et al. ........ 604/385.04 |
| 2006/0142710 | A1 * | 6/2006 | Kigata et al. .................. 604/361 |
| 2006/0149202 | A1 * | 7/2006 | Cardin et al. ............ 604/385.04 |
| 2008/0015536 | A1 * | 1/2008 | Digiacomantonio et al. ........................ 604/385.04 |

FOREIGN PATENT DOCUMENTS

| JP | 4-152946   | 5/1992  |
| JP | 5-086322   | 11/1993 |
| JP | 7-506037   | 7/1995  |
| JP | 2003-111799 | 4/2003  |
| JP | 2004-113590 | 4/2004  |
| JP | 2004-290602 | 10/2004 |

* cited by examiner

*Primary Examiner* — Jackie Ho
*Assistant Examiner* — Aundria Hairell
(74) *Attorney, Agent, or Firm* — Jordan and Hamburg LLP

(57) ABSTRACT

Provided is a sanitary napkin having wings that can be easily attached by being properly folded back at correct positions without causing problems in the wing-like flaps, such as adhesion of adhesive surfaces to each other and wrong adhesion. In a sanitary napkin including wing-like flaps disposed on both sides of a main body to be fixed to an undergarment so as to wrap around a crotch portion of the undergarment when it is worn, each wing-like flap has a front outline extending outward from the main body and a back outline extending outward from the main body and is designed such that the angle β formed by the width-direction line of the sanitary napkin and the back outline is larger than the angle θ formed by the width-direction line of the sanitary napkin and the front outline and that the gravity center of the wing-like flap is located more toward the front of the sanitary napkin than the center point of the boundary line of the root of the wing-like flap W and the main body.

10 Claims, 10 Drawing Sheets

ABSORBENT ARTICLE HAVING ANGLED FLAPS

BACKGROUND OF THE INVENTION

The present invention relates to an absorbent article having wing-like flaps that are used to wrap around the crotch portion of an undergarment for fixing the absorbent article to the undergarment.

As absorbent articles for sanitary napkins, pantiliners, vaginal discharge sheets, incontinence pads, and the like, conventionally known is, for example, as shown in FIG. 10, an absorbent article N that has an absorber 52 formed of, for example, cotton-like pulp interposed between a liquid-impermeable back sheet 50 formed of, for example, a polyethylene sheet or a polyethylene laminated nonwoven fabric and a liquid-permeable top sheet 51 formed of, for example, a nonwoven fabric or a porous plastic sheet.

In such a type of the absorbent article N, in order to prevent displacement when it is being worn, for example, the absorbent article is provided with one or more lines of adhesive layers 53, 53 on the surface not brought into contact with the skin (outer surface), wing-like flaps W, W on both sides in the longitudinal direction of the napkin body so as to extend outward, and adhesive layers 54, 54 on the surfaces (outer surfaces) of the wing-like flaps W, W on the liquid-impermeable back sheet 50 (see, for example, Patent Documents 1 and 2).

In order to fix the absorbent article N to an undergarment 60, as shown in FIG. 11, the absorbent article N is put on an appropriate local portion of the undergarment 60, the wing-like flaps W, W protruding sideward are allowed to protrude outward from the undergarment, both the wing-like flaps W, W are folded back at the folding lines RL, RL so as to wrap around the crotch portion of the undergarment and thereby to adhere to the outer surface of the crotch portion of the undergarment 60, and then the undergarment is worn on the body. Background Prior Art is as Follows:

[Patent Document 1] JP-A-2003-111799
[Patent Document 2] JP-A-2004-113590

SUMMARY OF INVENTION

The wing-like flap W can be highly effective means to help an absorbent article be fixed to shorts, but the wing-like flap W may, carelessly, be only partially folded back. In such a case, adhesive surfaces adhere to each other to cause wrinkles or raised portions, or the partially folded back wing-like flap W adheres to an adhesive surface, which is not intended and appropriate. In addition, when the wing-like flap W is not properly folded back along the folding line RL, but is wrongly folded back along a slant folding line, problems are caused such as uncomfortable feeling in the thigh by the protruding portion due to such folding back.

Accordingly, a main object of the present invention is to provide an absorbent article that can be easily attached by properly folding back the wing-like flaps at right folding positions without causing trouble such as adhesion of adhesive surfaces to each other and adhesion at an incorrect location.

In order to solve the above-mentioned problems, the invention in a first aspect thereof provides an absorbent article comprising wing-like flaps that are respectively formed on both sides of a main body in which an absorber is interposed between a liquid-permeable top sheet and a liquid-impermeable back sheet and that are fixed to an undergarment so as to wrap around a crotch portion of the undergarment when the article is worn, wherein the wing-like flaps have a front outline extending outward from the main body and a back outline extending outward from the main body; and the wing-like flaps are designed such that an angle formed by the width-direction line of the absorbent article and the back outline is larger than the angle formed by the width-direction line of the absorbent article and the front outline and such that the gravity center of each wing-like flap is located more toward the front of the absorbent article than the center of the boundary line between the root of the wing-like flap and the main body.

In the first aspect of invention, the planar shape of the wing-like flap is designed such that the angle (β: see FIG. 4) formed by the width-direction line of the absorbent article and the back outline is larger than the angle (θ: see FIG. 4) formed by the width-direction line of the absorbent article and the front outline and such that the gravity center of each wing-like flap is located more toward the front of the absorbent article by ΔS (see FIG. 4) than the center of the boundary line of the root of the wing-like flap and the main body. In other words, instead of conventional isosceles trapezoidal flaps, substantially triangular or asymmetric trapezoidal flaps in which the slope of the back edge of each flap is steeper than that of the front edge are used. By forming the outer shape as such, as described below, the absorbent article can be easily attached by properly folding back the wing-like flaps at correct folding positions without causing troubles such as adhesion of adhesive surfaces to each other and adhesion at undesired locations.

A second aspect of the invention provides the absorbent article according to the first aspect, wherein a difference between the angle formed by the width-direction line of the absorbent article and the front outline and the angle formed by the width-direction line of the absorbent article and the back outline is 30° or more.

The second aspect of the invention specifically defines the shape of the wing-like flap. The desired purpose of the present invention can be effectively achieved by designing the shape such that the difference between the angle θ formed by the width-direction line of the absorbent article and the front outline and the angle β formed by the width-direction line of the absorbent article and the back outline is 30° or more.

The third aspect of the invention provides the absorbent article according to either the first aspect or the second aspect, wherein the wing-like flaps have a substantially triangular or substantially asymmetric trapezoidal planar shape.

In the invention of the third aspect, the outer shape of the wing-like flap when it is schematically drawn is substantially triangular or substantially asymmetric trapezoidal.

The invention according to a fourth aspect thereof provides the absorbent article according to any one of the first to third aspects, wherein the wing-like flap has an extending length longer than the crotch width of shorts.

In the invention of the fourth aspects the absorbent article can be firmly fixed to shorts with the wing-like flaps having an extending length longer than the crotch width of the shorts.

The invention according to a fifth aspect thereof provides the absorbent article according to any of the first to fourth aspects, wherein the wing-like flaps have a rear surface provided with an adhesive layer having a shape in which the width in the longitudinal direction of the absorbent article decreases from the base of the flap toward the end of the flap.

In the invention of the fifth aspect, the adhesive layer provided on the rear face of each wing-like flap is shaped such that the width in the longitudinal direction of the absorbent article decreases from the base of the flap toward the end of the flap, specifically, shaped so as to be a substantially triangular or a substantially isosceles or asymmetric trapezoidal shape, and thereby adhesion of adhesive surfaces to each other and wrong adhesion are prevented from occurring.

The invention of the sixth aspect provides the adsorbent article according to any of the first to fifth aspects, wherein the wing-like flaps are colored at their end portions.

In a sixth aspect of the invention, the end of each wing-like flap is colored, and thereby the end can be visually confirmed to prevent wrong wearing.

The invention according to a seventh aspect thereof provides the absorbent article according to any of the first to sixth aspects, wherein at least the wing-like flaps are constituted of a material stretchable in the longitudinal direction and the width direction of the absorbent article.

In the seventh aspect of the invention, since at least the wing-like flaps are constituted of a material stretchable in the longitudinal direction and/or the width direction of the absorbent article, the wing-like flaps follow movement of the body to reduce the stress, which provides comfortable wearing and prevents displacement.

According to the present invention as described above, the absorbent article can be easily attached by properly folding back the wing-like flaps at correct folding positions without causing trouble such as adhesion of adhesive surfaces to each other and wrong adhesion.

DETAILED DESCRIPTION OF THE INVENTION

Embodiments of the present invention will be described in detail below with reference to drawings.

Figure 1:
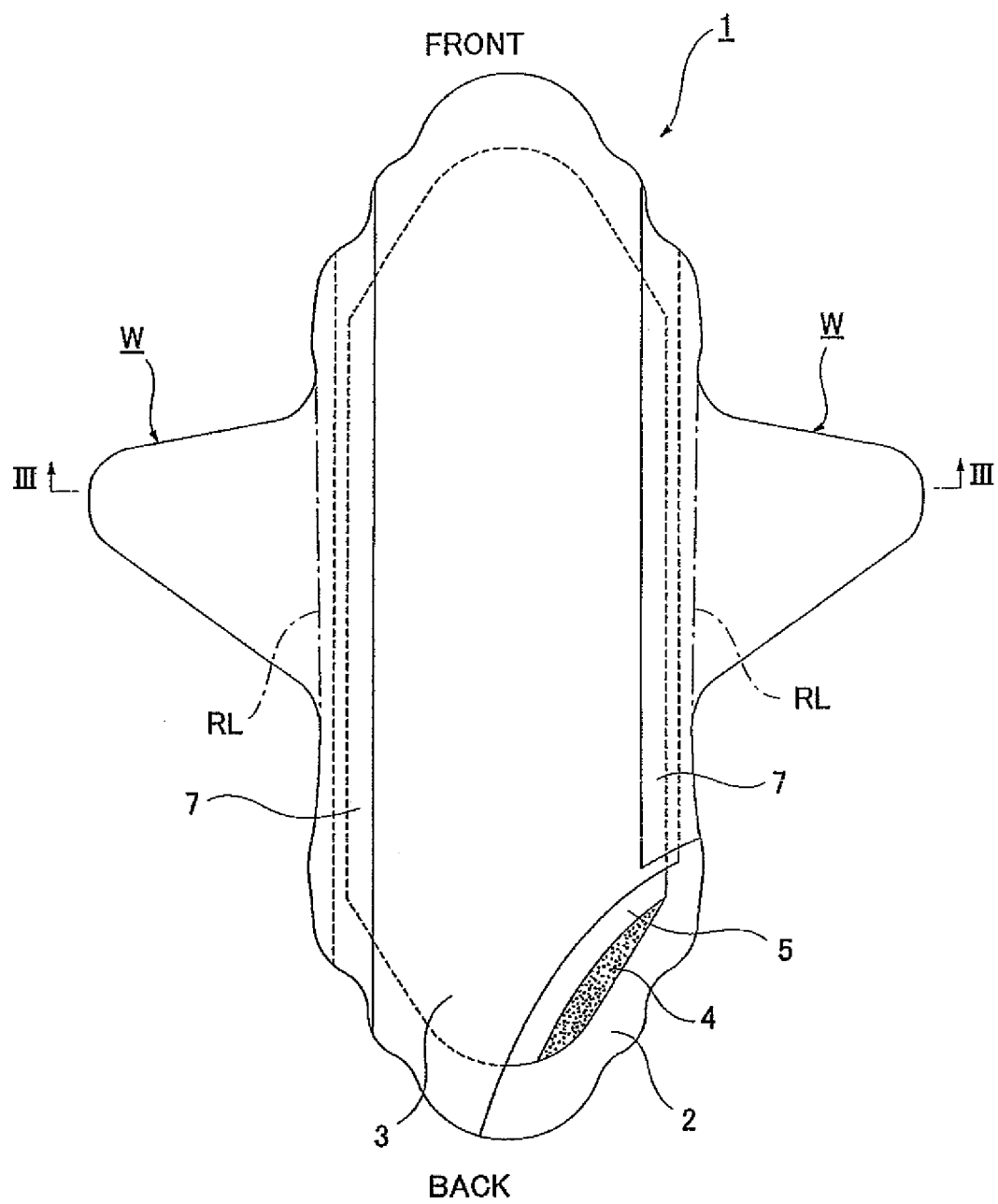
FIG. 1 is a partially broken development view of a sanitary napkin 1 according to the present invention.
Figure 2:
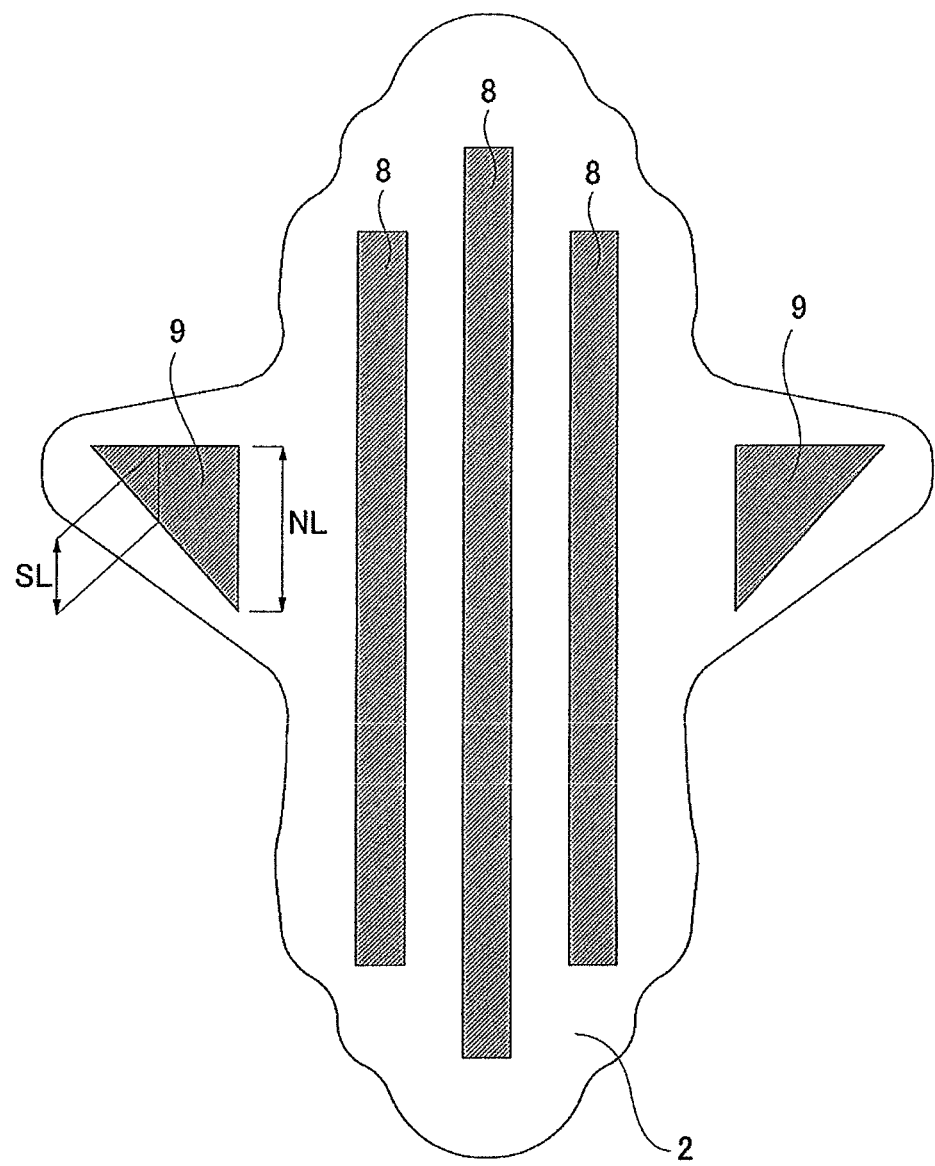
FIG. 2 is the back side view of the sanitary napkin 1.
Figure 3:
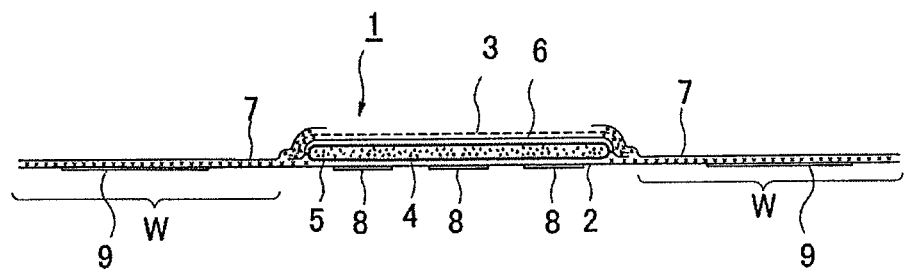
FIG. 3 is a fragmentary view taken along the III-III line in FIG. 1.

FIG. 1 is a partially broken development view of a sanitary napkin 1 according to the present invention, FIG. 2 is the back side view thereof, and FIG. 3 is a fragmentary view taken along the line in FIG. 1.

Sanitary Napkin 1

The sanitary napkin 1 is constituted of a liquid-impermeable back sheet 2 composed of, for example, a polyethylene sheet or a polypropylene sheet; a liquid-permeable top sheet 3 that allows menstrual blood, vaginal discharge, or the like to rapidly permeate; an absorber 4 composed of, for example, cotton-like pulp or synthetic pulp and interposed between the sheets 2 and 3; creped paper 5 surrounding the absorber 4 for maintaining the shape and increasing the diffusing ability of the absorber 4; a second sheet 6 composed of a hydrophilic nonwoven fabric and interposed between the liquid-permeable top sheet 3 and the crepe paper 5; and side nonwoven fabrics 7, 7 respectively disposed at both sides of the top face along the longitudinal direction. The outer edges of the liquid-impermeable back sheet 2 and the liquid-permeable top sheet 3 are bonded to each other at the upper and lower ends in the area surrounding the absorber 4 with an adhesive such as hot melt or by adhesion means such as heat sealing, and, at both outer sides, the liquid-impermeable back sheet 2 protruding sidewardly beyond the absorber 4 and each side nonwoven fabric 7 are bonded to each other with an adhesive such as hot melt or by adhesion means such as heat sealing.

The structure of the sanitary napkin 1 will be further described in detail below.

As the liquid-impermeable back sheet 2, a sheet material having at least a waterproof property, for example, an olefin-based resin sheet such as polyethylene or polypropylene, is used. In addition, used is a laminated nonwoven fabric in which a nonwoven fabric is laminated to a polyethylene sheet or the like, or a nonwoven sheet provided with a waterproof film for ensuring a substantial liquid-impermeable property (in such a case, the waterproof film and the nonwoven fabric constitute a liquid-impermeable back sheet). Recently, from the viewpoint of preventing a damp or humid feel, a material having moisture permeability tends to be used. Such a waterproof and moisture-permeable sheet material is a micro-porous sheet that is prepared by melt-kneading an inorganic filler in an olefin-based resin such as polyethylene or polypropylene and forming it into a sheet and then uniaxially or biaxially stretching the sheet.

The liquid-permeable top sheet 3 is preferably made of porous or nonporous nonwoven fabric or a porous plastic sheet. Examples of a fibrous base material that is used for constituting the nonwoven fabric include as well as synthetic fiber such as olefin-based (such as polyethylene or polypropylene), polyester-based, and polyamide-based synthetic fiber, recycled fiber such as rayon or cupra, and natural fiber such as cotton, and a nonwoven fabric prepared by any suitable processing method such as spunlacing, spunbonding, thermal bonding, meltblowing, or needle punching can be used. Among these processing methods, spunlacing makes a nonwoven fabric excellent in flexibility and drape property, and thermal bonding makes a nonwoven fabric excellent in bulk and softness. In addition, it is desirable that the liquid-permeable top sheet 3 is provided with various types of embossments from the upper face to increase absorption efficiency by accelerating accumulation of body fluid and thereby prevent side leakage.

The absorber 4 interposed between the liquid-impermeable back sheet 2 and the liquid-permeable top sheet 3 is constituted of, for example, fluff-like pulp and a water-absorbing polymer. The water-absorbing polymer, for example, in a form of granular powder is mixed in pulp constituting the absorber. Examples of the pulp include those composed of cellulose fiber such as chemical pulp made from wood and melting pulp and those composed of artificial cellulose fiber such as rayon and acetate. Softwood pulp has a longer fiber length than that of hardwood pulp and is preferably used in the light of function and cost performance. When crepe paper 5 surrounding the absorber 4 as in this embodiment is used, the crepe paper 5 is accordingly interposed between the liquid-permeable top sheet 3 and the absorber 4. Consequently, the crepe paper 5, which is excellent in absorbability, allows rapid diffusion of body fluid and prevents returning back of menstrual blood and the like.

The second sheet 6 interposed between the liquid-permeable top sheet 3 and the crepe paper 5 is composed of nonwoven fabric with hydrophilicity. The examples of the material of the nonwoven fabric include olefin-based (such as polyethylene or polypropylene), polyester-based, or polyamide-based synthetic fiber, recycled fiber such as rayon or cupra, or natural fiber such as cotton, and a nonwoven fabric prepared by any suitable processing method such as spunlacing, spunbonding, thermal bonding, meltblowing, or needle punching can be used. The hydrophilicity can be provided, applying capillarity, by making the synthetic fiber swollen or porous with the methods such as, polymerization in the presence of a compound having hydrophilic group such as an oxidation product of polyethylene glycol during a process of producing the synthetic fiber, or treating a surface with a metal salt such as stannic chloride for partially dissolving and making the surface porous and depositing a metal hydroxide.

Furthermore, the sanitary napkin 1 is provided with side nonwoven fabrics 7, 7 at both sides of the top surface along the longitudinal direction for approximately the entire length of the napkin 1. The side nonwoven fabrics 7, 7 partially extend sideward and form the wing-like flaps W, W together with parts of the liquid-impermeable back sheet 2 similarly extending sideward. The wing-like flap W will be described in detail below.

The side nonwoven fabric 7 is formed of a water repellency-treated nonwoven fabric or hydrophilicity-treated nonwoven fabric, according to an important function. For example, when a function of preventing infiltration of menstrual blood, vaginal discharge, or the like or a function increasing texture is emphasized, it is desirable to use a nonwoven fabric provided with water repellency by being coated with, for example, a silicon-based, paraffin-based, alkyl chromic chloride-based water repellent agent. When absorbability of the wing-like flaps W, W for menstrual blood or the like is emphasized, used is a hydrophilicity-treated nonwoven fabric that is imparted with the hydrophilicity, applying capillarity, by making the synthetic fiber swollen or porous with the methods such as, polymerization in the presence of a compound having hydrophilic group such as an oxidation product of polyethylene glycol during a process of producing the synthetic fiber, or treating a surface with a metal salt such as stannic chloride for partially dissolving and making the surface porous and depositing a metal hydroxide.

As shown in FIG. 2, the main body having the absorber 4 interposed between the liquid-permeable top sheet 3 and the liquid-impermeable back sheet 2 is provided with a plurality of main body displacement-preventing adhesive layers 8, 8, and 8, three lines of adhesive in the drawing, by an arbitrary application pattern, on the face not brought into contact with the skin for being fixed to a undergarment, and the main body displacement-preventing adhesive layers 8, 8, . . . , and 8 are covered with a release material (not shown) for the main body. In addition, the wing-like flaps W, W are each provided with a wing displacement-preventing adhesive layer 9 on the surface on the liquid-impermeable back sheet 2. The wing displacement-preventing adhesive layers 9, 9 are each covered with a release material (not shown) for the wing. It is desirable that the release material for the main body and the release material for the wing disposed in the transverse direction be joined to each other at the crossing portion so that the release materials can be removed at one time. The wing-like flaps W, W may be folded to the liquid-permeable top sheet 3, so-called front folding, or may be folded to the liquid-impermeable back sheet 2, so-called back folding, in an individually packaged form. In addition, the release material covering the wing displacement-preventing adhesive layers 9, 9 may be separated into left and right release materials instead of one piece of the release material.

The release material may be paper or a plastic sheet provided with mold release treatment by applying or spraying mold release solution such as a silicon-based resin, a fluorine-based resin, or a tetrafluoroethylene-based resin on the surface that is brought into contact with the displacement-preventing adhesive layers 8 and 9.

As the adhesive for forming the displacement-preventing adhesive layers 8 and 9, for example, an adhesive whose main component is any of a styrene-based polymer, an adhesion-imparting agent, and a plasticizing agent can be preferably used. Examples of the styrene-based polymer include styrene-ethylene-butylene-styrene block copolymers, styrene-butylene-styrene block copolymers, and styrene-isobutylene-styrene copolymers. These may be used alone or as a polymer blend of two or more thereof. Among them, from the standpoint of favorable thermal stability, the styrene-ethylene-butylene-styrene block copolymers are preferred. As the adhesion-imparting agent and the plasticizing agent, one that is solid at ordinary temperature is preferably used. Examples of the adhesion-imparting agent include C5-based petroleum resins, C9-based petroleum resins, dicyclopentadiene-based petroleum resins, rosin-based petroleum resins, polyterpen resins, and terpene phenol resins. Examples of the plasticizing agent include, in addition to monomer plasticizing agents such as triphenyl phosphate, dibutyl phthalate, and dioctyl phthalate, polymer plasticizing agents such as vinyl polymers and polyesters.

Wing-like Flap W

Figure 4:
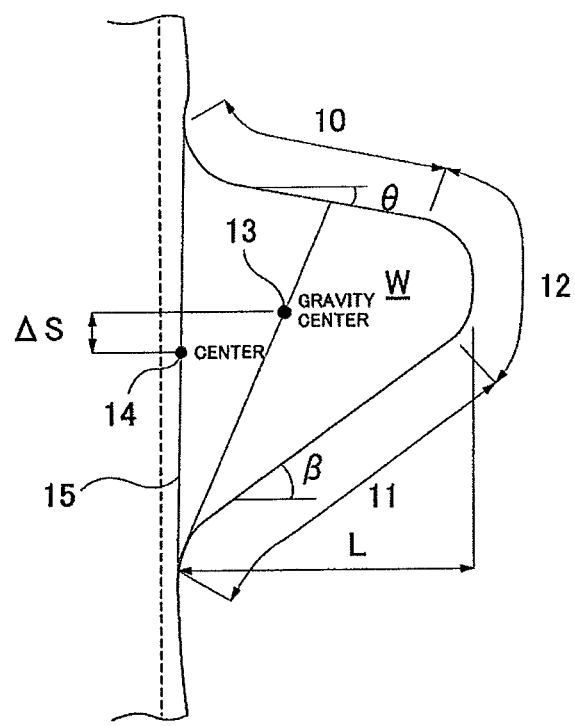
FIG. 4 is an enlarged plan view of a main section of the wing-like flap.
Figure 7A:
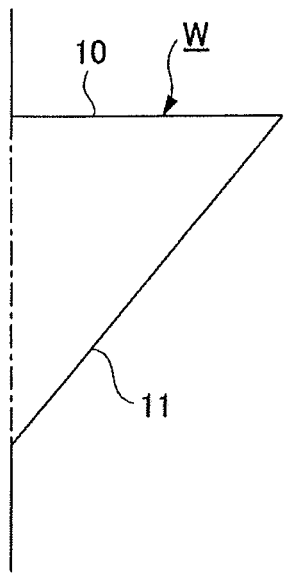
FIGS. 7(A) and 7(B) are schematic diagrams showing planar shapes of the wing-like flaps according to the present invention.
Figure 7B:
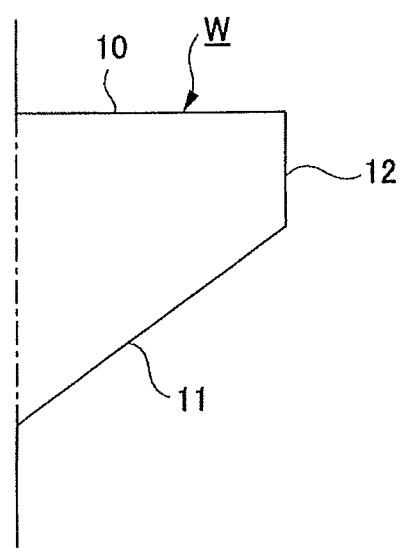

As shown in FIG. 4 in detail, the wing-like flap W has an outer shape formed of a front outline 10 extending outward from the main body, a back outline 11 extending outward from the main body, and end outline 12 connecting the front outline 10 and the back outline 11. In the sanitary napkin 1, the wing-like flap W has a shape designed such that the angle $\beta$ formed by the width-direction line of the sanitary napkin 1 and the back outline 11 is larger than the angle $\theta$ formed by the width-direction line of the sanitary napkin 1 and the front outline 10 and that the gravity center 13 of the wing-like flap W is located more toward the front of the absorbent article by $\Delta S$ than the central point 14 of the boundary line 15 of the root of the wing-like flap W and the main body. When a shape satisfying the above-mentioned requirements is schematically drawn, the shape becomes a substantially triangular shape shown in FIG. 7(A) or a substantially asymmetric trapezoidal shape shown in FIG. 7(B). When the shape is substantially triangular, the end outline 12 connecting the front outline 10 and the back outline 11 is not present. The front outline 10, the back outline 11, and the end outline 12 are each not necessarily a straight line and may be a wavelike line, a curved line, or a combination thereof. In such a case, the angle $\theta$ and $\beta$ may be each a gradient of a center line of the wavelike or curved outline.

Desirably, the angle $\theta$ formed by the width-direction line of the sanitary napkin 1 and the front outline 10 is approximately 0 to 15°, and the angle $\beta$ formed by the width-direction line of the sanitary napkin 1 and the back outline 11 is approximately 30 to 50°. In such a case, the difference between the angle $\theta$ formed by the width-direction line of the sanitary napkin 1 and the front outline 10 and the angle β formed by the width-direction line of the sanitary napkin 1 and the back outline 11 is desirably 30° or more. An angle difference of 30° or more can secure a sufficient eccentric distance ΔS, and the sanitary napkin 1 can be properly worn in a right condition even if the wing-like flap is folded back with the hand while the hand is moving toward the front side, as described below.

Figure 10:
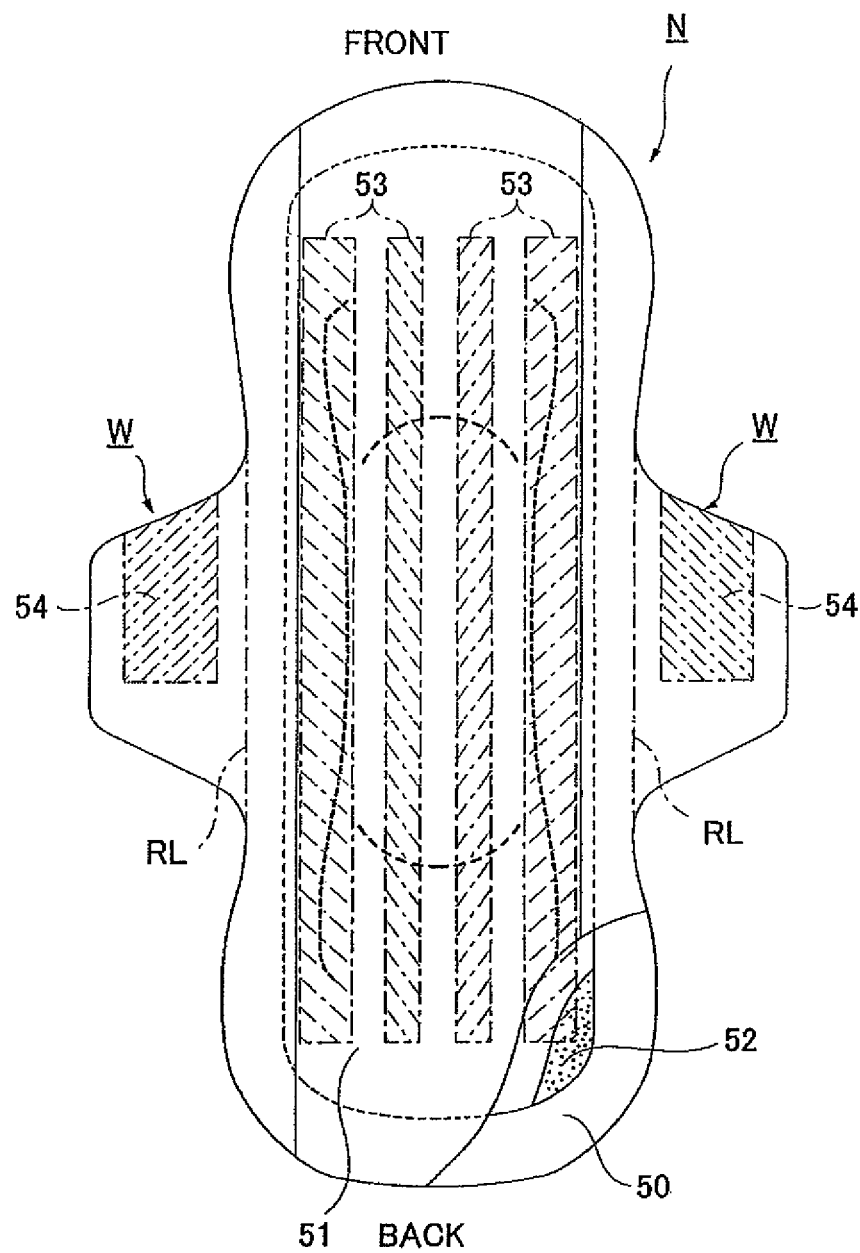
FIG. 10 is a development view of a conventional sanitary napkin N.
Figure 11:
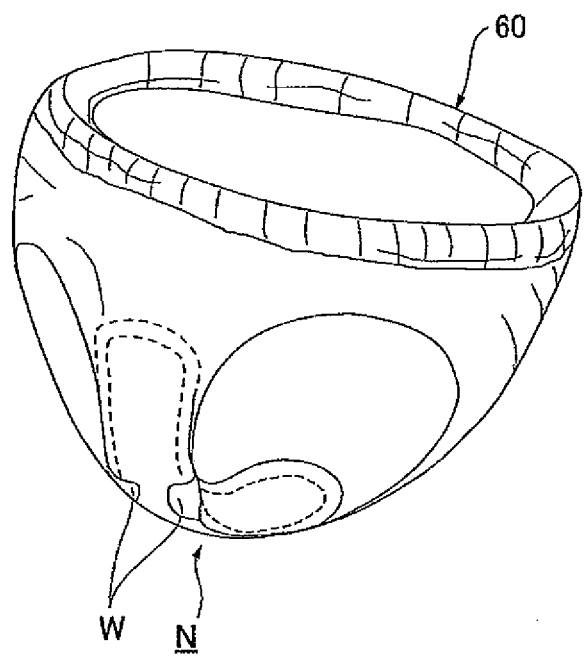
FIG. 11 is a view showing the state when the napkin N is worn.

The wing-like flap W having the above-described outer shape can achieve advantages such that an absorbent article can be easily attached by properly folding back the wing-like flaps at right folding positions without causing troubles such as adhesion of adhesive surfaces to each other and wrong adhesion. This point will be further described in detail by comparison to a conventional isosceles trapezoidal wing-like flap W (see FIG. 10).

First, when a sanitary napkin 1 is attached to shorts 20 in the state that a woman is sitting on, for example, a toilet seat, as shown in FIG. 5, the napkin 1 is attached to the shorts 20, which are pulled down, at the front of the body.

Figure 5A:
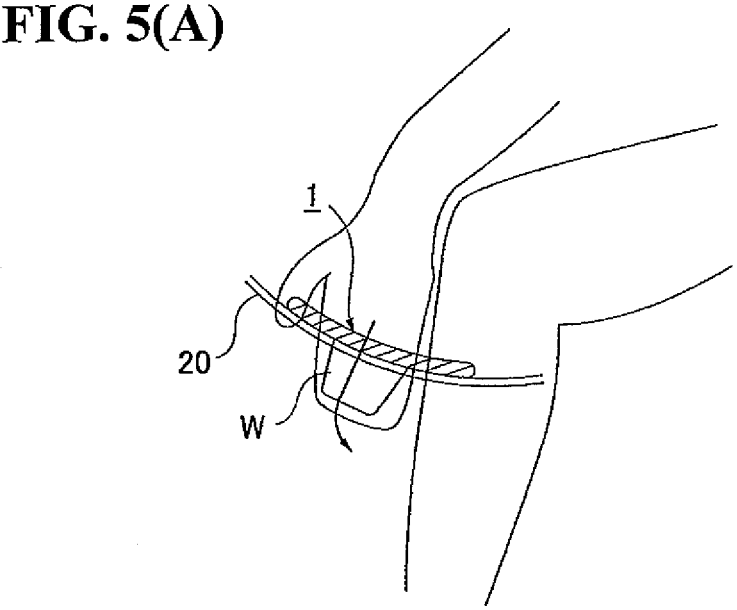
FIGS. 5(A) and 5(B) show how to wear a napkin and include a case of a conventional wing-like flap, FIG. 5(A), and a case of a wing-like flap according to the present invention, FIG. 5(B).
Figure 5B:
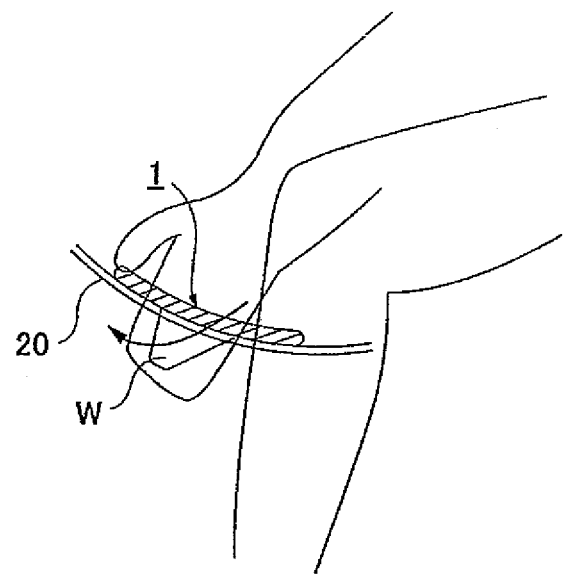

As shown in FIG. 5(A), the conventional isosceles trapezoidal wing-like flap W has a structure such that the napkin is properly worn by folding back the wing-like flap toward the directly below direction with the hand placed on both sides of the napkin. However, since the wearing is performed at the front of the body, the hand moves toward the front side (FIG. 5(B)), if attention is not paid, to cause problems that the wing-like flap is partially folded back so that adhesive surfaces adhere to each other to cause wrinkles or raised areas or that the wing-like flap W is intermediately folded back and adheres to the adhesive layer to cause wrong adhesion. In addition, the wing-like flap may, undesirably, be folded back along a slant folding line. Accordingly, in the present invention, as shown in FIG. 5(B), the wing shape is designed such that the wing-like flap can be properly worn in a right condition even if the wing-like flap is folded back with the hand in while the hand moving toward the front.

Figure 6A:
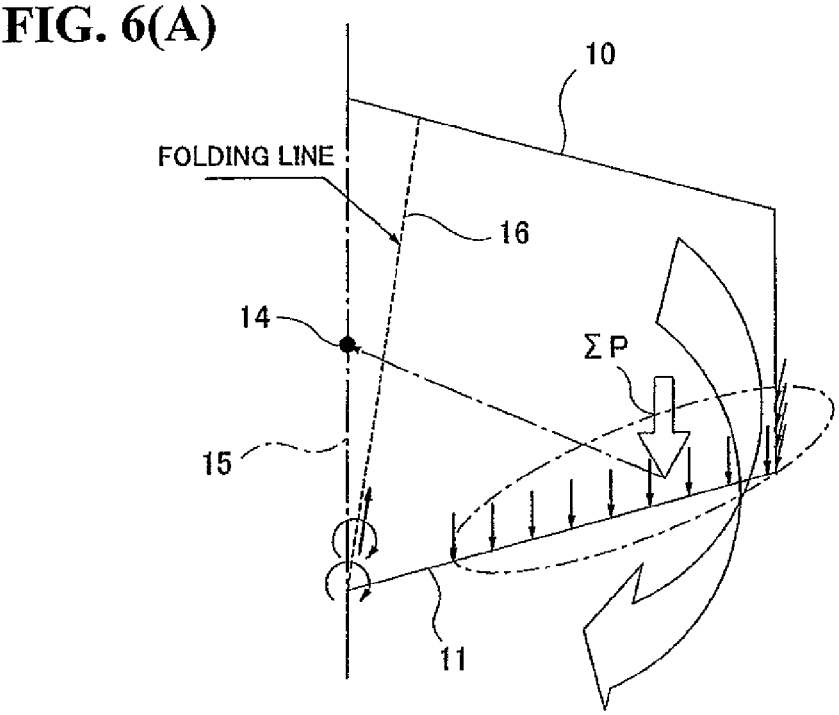
FIGS. 6(A) and 6(B) show an acting force mechanism when a wing-like flap is folded back and include a case of a conventional wing-like flap, FIG. 6(A), and a case of a wing-like flap according to the present invention, FIG. 6(B).

FIG. 6(A) shows an acting force mechanism when the conventional isosceles trapezoidal wing-like flap W is folded back. When the wing-like flap is folded back with the hand moving toward the front, in an assumed concentrated load ΣP of distributed loads provided that the loads act downwardly along from the back outline of the wing-like flap W to the end, the base point of a moment generated by the concentrated load ΣP is the central point 14 of the boundary line 15 of the wing-like flap. Therefore, twists occur when the wing-like flap W is folded back, and the folding line 16 that is gradually formed from the base of the back outline 11 slants outward.

Figure 6B:
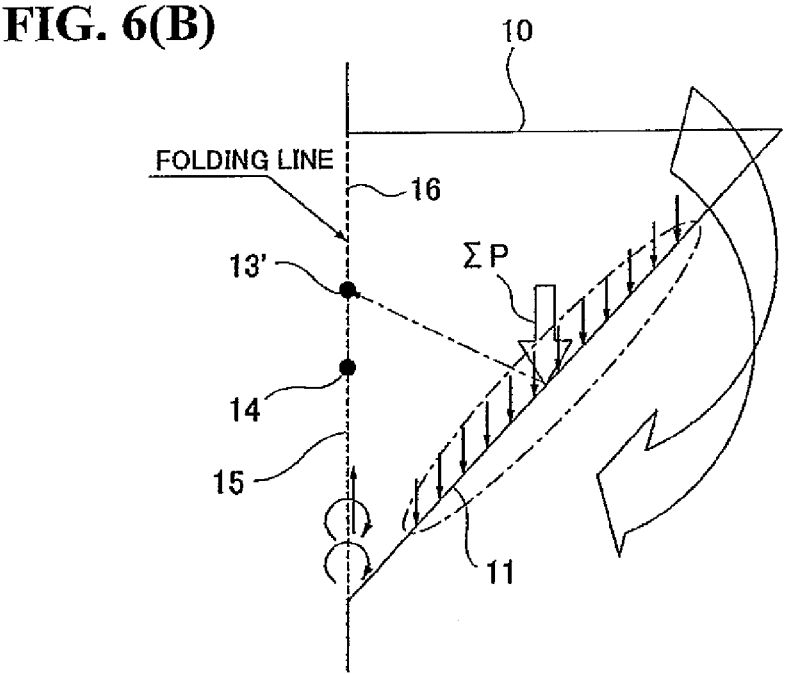

On the other hand, in the present invention, as shown in FIG. 6(B), in an assumed concentrated load ΣP of distributed loads provided that the loads act downwardly in the central portion of the sloping back outline 11, the base point of a moment generated by the concentrated load ΣP becomes the gravity center cutoff point 13' (1:2 cutoff point of the boundary line 15) that is shifted more toward the front of the absorbent article than the central point 14 of the boundary line 15 of the wing-like flap. Therefore, no twists occur when the wing-like flap W is folded back, and thereby the folding line 16 that is gradually formed from the base of the back outline 11 coincides with the boundary line 15, and the wing-like flap W is folded back at a right folding position.

In addition, since the slope of the back outline 11 of the wing-like flap W is steep, the wing-like flap W is properly folded at the folding line RL, without causing troubles such as adhesion of adhesive surfaces to each other and wrong adhesion.

The extending length L of the wing-like flap W is preferably 40 to 50 mm so that it is longer than the crotch width of shorts 20. By designing the extending length longer than the crotch width of the shorts 20, the sanitary napkin can be firmly fixed to the shorts.

Furthermore, the wing displacement-preventing adhesive layer 9 provided on the back face of the wing-like flap W, as shown in FIG. 2, preferably has a shape in which the width in the longitudinal direction of the napkin 1 decreases from the base NL toward the end SL, specifically, a substantially triangular or a substantially isosceles or asymmetric trapezoidal shape. By making so, adhesion of adhesive surfaces to each other and wrong adhesion hardly ever occur when the wing-like flap W is folded back.

Figure 8:
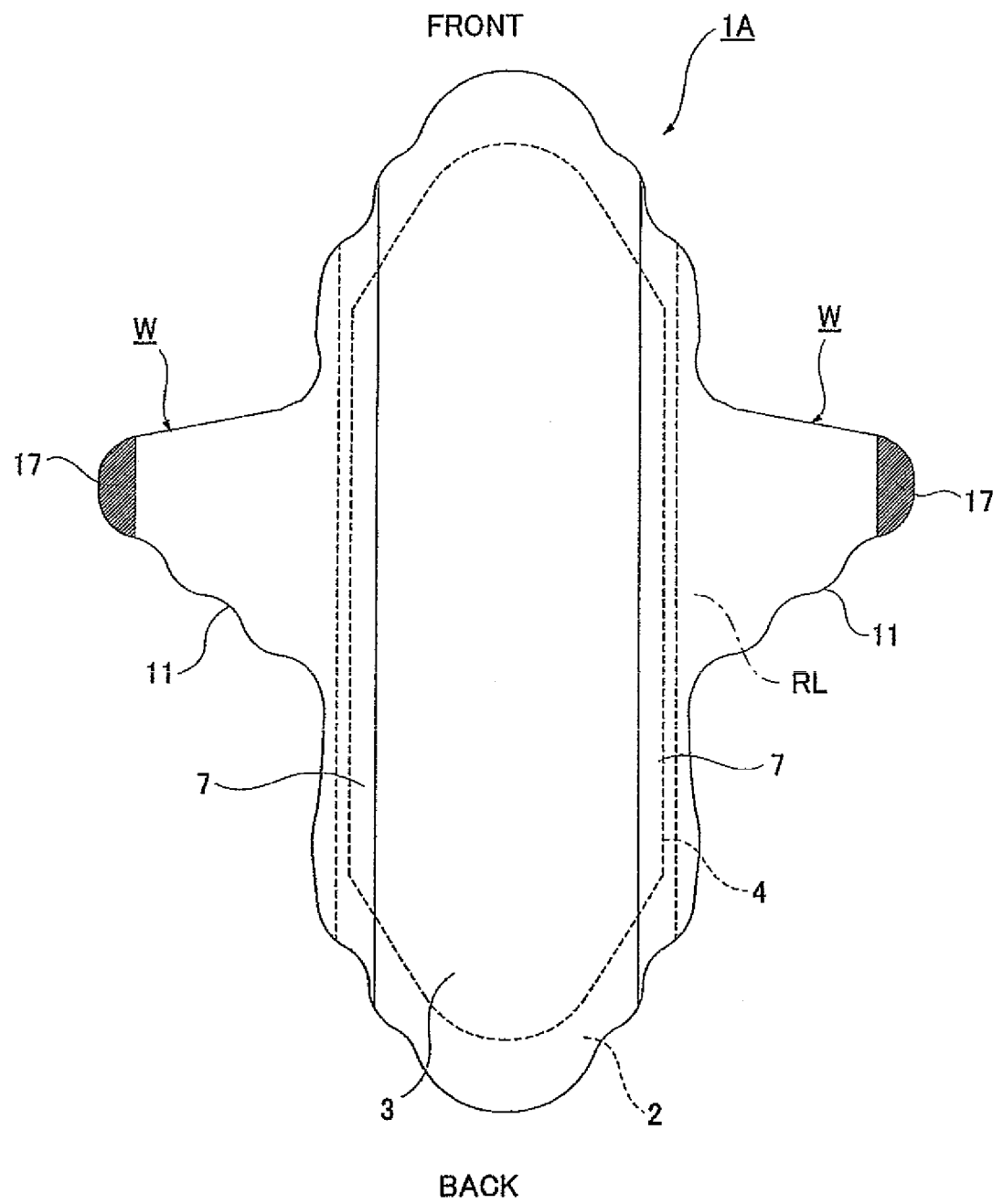
FIG. 8 is a plan view showing a modification of a sanitary napkin according to the present invention.

Other Embodiments (1) As shown in FIG. 8, the ends of the wing-like flaps W, W are provided with color 17, and thereby the ends can be visually confirmed to prevent wrong wearing.

(2) As shown in FIG. 8, the back outline 11 of the wing-like flap W may be a wavelike curved line composed of small convex lines and small concave lines. In such a case, it is easy to distinguish the front from the back, and the slope of the back outline 11 can be emphasized visually.

(3) When the wing-like flap W is constituted with a material stretchable in the longitudinal and/or the width direction of the napkin, the wing-like flap W follows movement of the body to reduce the stress, which provides comfortable wearing and prevents displacement. Specifically, as the side nonwoven fabric 7, used is a side nonwoven fabric having stretchability, specifically, for example, a nonwoven fabric constituted of long fiber composed of an elastic resin material that is easily deformed plastically and reversibly, such as polyurethane, or a nonwoven fabric exhibiting stretchability by that a zig-zag or spiral crimp is formed and is extended whereas the fiber diameter of the fiber itself is not changed when the fabric is extended; as the liquid-impermeable back sheet 2, used is a stretchable plastic film; and, as a result, the wing-like flaps W, W are provided with stretchability and are allowed to follow movement of the body.

Figure 9A:
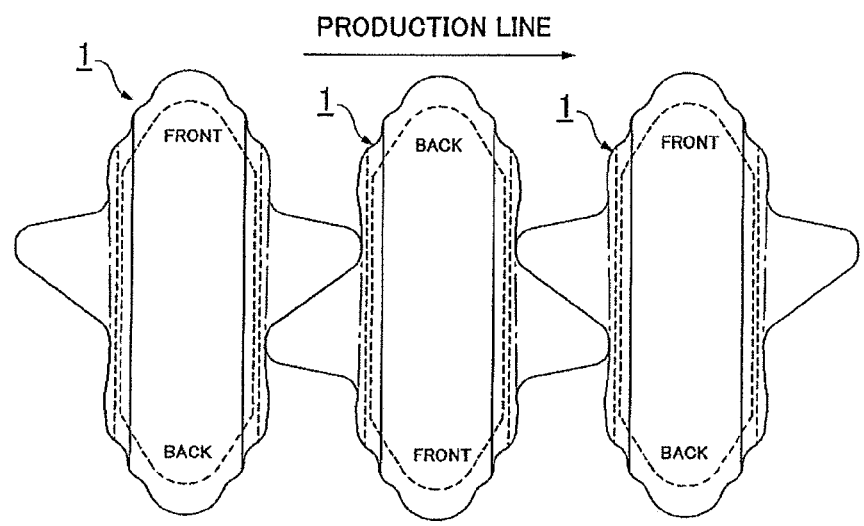
FIGS. 9(A) and 9(B) are napkin-assembly flow diagrams showing how to produce the sanitary napkins 1 according to the present invention.
Figure 9B:
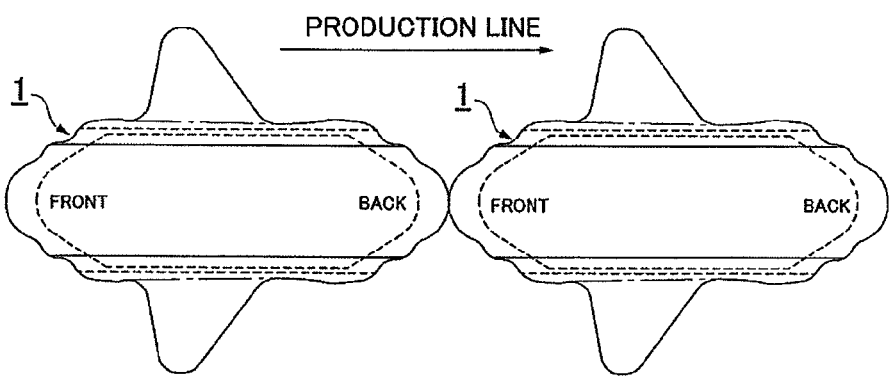

(4) The sanitary napkin 1 can be produced by a vertical flow system shown in FIG. 9(B), but, as shown in FIG. 9(A), in a horizontal flow system, a large number of napkins 1, 1, . . . , and 1 can be efficiently produced with small amounts of materials by alternately arranging the napkins normally and reversely. In such a case, the outlines of the wing-like flaps are determined so that the back outline of the wing-like flap W of the normally arranged napkin 1 and the back outline of the wing-like flap W of the reversely arranged napkin 1 coincide with each other under conditions that absorbers 4 are aligned on the same straight line without displacement to right and left with respect to the production line direction.

The invention claimed is:

1. An absorbent article comprising wing-like flaps that are respectively disposed on both sides or a main body in which an absorber is interposed between a liquid-permeable top sheet and a liquid-impenetrable back sheet and that are to be fixed to an undergarment so as to wrap around a crotch portion of the undergarment when the article is worn, wherein the wing-like flaps have a front outline extending outward from the main body and a back outline extending outward from the main body;

wherein the wing-like flaps are configured so that an angle formed by a first width-direction line of the absorbent article and the back outline is larger than an angle formed by a second width-direction line of the absorbent article and the front outline and that a gravity center of the wing-like flap is located more toward the front of the undergarment than a center of a boundary line of a root of the wing-like flap and the main body;

wherein the back outline is a wavelike line formed by a combination of convex curves and concave curves; and wherein for each said one or the wing-like flaps, the back outline is shaped so as to coincide with a back outline of a reversely arranged same article aligned side by side along a same straight line parallel to said width direction line so that the front edge of the main body of the absorbent article and the back edge of the main body of the reversely arranged same article are arranged along a common straight line parallel to said width direction line.

2. The absorbent article according to claim 1, wherein a difference between the angle formed by the width-direction line of the absorbent article and the front outline and the angle formed by the width-direction line of the absorbent article and the back outline is at least 30°.

3. The absorbent article according to claim 1, wherein the wing-like flaps have a substantially triangular or substantially asymmetric trapezoidal planar shape.

4. The absorbent article according to claim 1, wherein the wing-like flaps have a back surface provided with an adhesive layer having a shape in which a width in the longitudinal direction of the absorbent article decreases from a base of the flap toward an end of the flap.

5. The adsorbent article according to claim 1, wherein the wing-like flaps are colored at their end portions.

6. The absorbent article according to claim 1, wherein at least the wing-like flaps are constituted of a material stretchable in the longitudinal direction and/or the width direction of the absorbent article.

7. The absorbent article according to claim 1, wherein an end portion of each one of said wing-like flaps is of a different color than a remaining area of a same surface of said one wing-like flap to identify correct wearing of the absorbent article.

8. The absorbent article according to claim 1, wherein for each said one of the wing-like flaps, the back outline has a linear portion shaped so as to coincide with a back outline of a reversely arranged same article aligned side by side along a same straight line.

9. The absorbent article according to claim 1, wherein an end portion of each one of said wing-like flaps is of a different color than a remaining area of a same surface of said one wing-like flap to identify correct wearing of the absorbent article.

10. An absorbent article comprising:

a main body;

wing-like flaps respectively disposed to each side of the main body, and that are adapted to be fixed to an undergarment with which the absorbent article is adapted to be worn by being configured to wrap around a crotch portion of the undergarment;

an absorber interposed between a liquid-permeable top sheet and a liquid-impermeable back sheet of the main body;

wherein the main body has a front to be arranged toward a front of the undergarment and a rear to be arranged toward a rear of the undergarment;

wherein each one of the wing-like flaps has a front outline extending outward from the main body and a back outline extending outward from the main body;

wherein each one of the wing-like flaps is configured so that an angle formed by a first width-direction line of the absorbent article and the back outline of said one wing-like flap is larger than an angle formed by a second width-direction line of the absorbent article and the front outline of said one wing-like flap, and that a gravity center of said one wing-like flap is located more toward the front of the undergarment than a center of a boundary line of a root of said one wing-like flap and said main body; and wherein for each said one of the wing-like flaps, the back outline is shaped so as to coincide with a back outline of a reversely arranged same article aligned side by side along a same straight line parallel to said first width-direction line so that the front edge of the main body of the absorbent article and the back edge of the main body of the reversely arranged same article are arranged along a common straight line parallel to said width direction line.

* * * * *